(12) United States Patent
Mester et al.

(10) Patent No.: US 11,674,165 B2
(45) Date of Patent: Jun. 13, 2023

(54) **ENRICHMENT OF *LISTERIA***

(71) Applicant: MERCK PATENT GMBH, Darmstadt (DE)

(72) Inventors: Patrick Julian Mester, Vienna (AT); Peter Rossmanith, Gaaden (AT); Nadine Weyhing-Zerrer, Pfinztal (DE); Tobais Gundolf, Vienna (AT); Susanne Fister, Vienna (AT); Anna Witte, Erlangen (DE)

(73) Assignee: MERCK PATENT GMBH, Darmstadt (DE)

( * ) Notice: Subject to any disclaimer, the term of this patent is extended or adjusted under 35 U.S.C. 154(b) by 764 days.

(21) Appl. No.: 16/460,289

(22) Filed: Jul. 2, 2019

(65) Prior Publication Data
US 2020/0010871 A1 Jan. 9, 2020

(30) Foreign Application Priority Data
Jul. 5, 2018 (EP) .................................... 18181827

(51) Int. Cl.
*C12Q 1/04* (2006.01)
*C12N 1/20* (2006.01)
*G01N 33/569* (2006.01)

(52) U.S. Cl.
CPC ............. *C12Q 1/045* (2013.01); *C12N 1/20* (2013.01); *C12N 2500/32* (2013.01); *C12N 2500/38* (2013.01); *C12N 2500/42* (2013.01); *C12N 2500/60* (2013.01); *C12N 2502/70* (2013.01); *C12N 2523/00* (2013.01)

(58) Field of Classification Search
CPC .. C12N 1/20; C12N 2500/32; C12N 2500/38; C12N 2500/42; C12N 2500/60; C12N 2502/70; C12N 2523/00; C12Q 1/045; C12Q 1/04; G01N 33/569; G01N 33/56911
See application file for complete search history.

(56) References Cited

U.S. PATENT DOCUMENTS

| | | |
|---|---|---|
| 6,416,970 B1 | 7/2002 | Schabert et al. |
| 10,619,181 B2 | 4/2020 | Moriyama et al. |
| 2018/0320213 A1 | 11/2018 | Moriyama et al. |

FOREIGN PATENT DOCUMENTS

| | | |
|---|---|---|
| EP | 0949266 A1 | 10/1999 |
| WO | 2012092181 A2 | 7/2012 |

OTHER PUBLICATIONS

Deng, "Protein adsorption and cellular uptake of AuNPs capped with alkyl acids of different length". RSC Advances (Issue 29, 2015). Retrieved from the internet: <URL: https://pubs.rsc.org/en/content/articlelanding/2015/ra/c4ra15960h> (Year: 2015).*
Burgess, "Effect of lauric acid and monolaurin on the multiplication of *Listeria monocytogenes* and *Listeria innocua* at 10° C. in bi-phasic systems". Doctoral Dissertation, Sheffield Hallam University (United Kingdom) 1999 <URL: http://shura.shu.ac.uk/19410/> (Year: 1999).*
Galbraith H, et al. "Antibacterial activity of long chain fatty acids and the reversal with calcium, magnesium, ergocalciferol and cholesterol." J Appl Bacteriol. Dec. 1971;34(4):803-13.
Search report in corresponding EP application 19184065.1 dated Oct. 29, 2019 (pp. 1-2).
Burgess A Pauline et al: Effect of lauric acid and monolaurin on the multiplication of *Listeria monocytogenes* and *Listeria innocua* at 10° C. in bi-phasic systems. (Jan. 1, 1999). pp. 1-155. Retrieved from the Internet: URL:http:jjshura.shu.ac.uk/19410/1/10694291.pdf (retrieved on Oct. 11, 2019].
Markus A. Keller et al: Studying fatty aldehyde metabolism in living cells with pyrene-labeled compounds, Journal of Lipid Research,vol. 53, No. 7, (Apr. 16, 2012) pp. 1410-1416. ISSN: 0022-2275.
Kinderlerer J L et al: Effect of 7-15 Medium-Chain Fatty Acids in Mould Ripened Cheese on the Growth of *Listeria* Monocytogenes, Journal of Dairy Research, Cambridge University Press, Cambridge, GB, vol. 63. No. 4. (Jan. 1, 1996). pp. 593-606, XP000960914. ISSN: 0022-0299.
Schaffer Shawn M et al: Microbiological safety of blue and cheddar cheeses containing naturally modified milk fat, Journal of Food Protection, vol. 58, No. 2, 1995, pp. 132-138, XP002794917, ISSN: 0362-028X.
Search report in corresponding EP application 19184065.1 dated Dec. 12, 2022 (pp. 1-8).
Liu Dongxin et al._ "Development of a Novel *Listeria* Enrichment Broth for the Isolation of Pathogenic *Listeria*" J. of Food Protection, vol. 80(10) 2017; pp. 1768-1776.
Supanivaton P. et al._ "Inhibitory effects of *Listeria* selective enrichment media on growth characteristics of *L. ivanovii*" Procedia Engineering 32, 2012; pp. 112-118.

* cited by examiner

*Primary Examiner* — Satyendra K Singh
(74) *Attorney, Agent, or Firm* — Millen, White, Zelano and Branigan, P.C.; Harry B. Shubin

(57) ABSTRACT

A method, a medium and a kit for the enrichment and detection of *Listeria* species, especially *Listeria monocytogenes*. The medium is an enrichment medium of C12 to C16 fatty acids and/or derivatives thereof.

6 Claims, 5 Drawing Sheets

4A

4B

5A

5B

ENRICHMENT OF LISTERIA

The present invention relates to a method, a medium and a kit for the enrichment and detection of *Listeria* species, especially *Listeria monocytogenes*. The medium is an enrichment medium comprising C12 to C16 fatty acids and/or derivatives thereof.

*Listeria* spp. bacteria are Gram-positive, non-spore forming and motile bacilli and can grow in a wide temperature range of about 4° C. to about 45° C. and a wide pH range of about 5.5 to about 9.5. The *Listeria* genus contains several species, including *Listeria monocytogenes, L. innocua, L. welshimeri, L. seeligeri, L. ivanovii, L. marthii* and *L. grayi*. Nearly all of the reported cases of human infections by bacteria belonging to the genus *Listeria* have been caused by *Listeria monocytogenes*. The immunocompromised, pregnant women, elderly, and neonates are susceptible to infection caused by this species. Typical symptoms of listeriosis include septicemia, meningitis and miscarriage.

Consumption of contaminated foods is the major cause of *Listeria* infection. There have been *Listeria*-induced infections caused by the consumption of contaminated foods, such as unpasteurized milk, contaminated cheese, coleslaw, and the like. Therefore, there is an increasing demand for a method of rapid, sensitive and accurate detection of *Listeria* in a sample, such as in a food, a surface wipe, or medical sample.

The detection of bacteria in food, water, waste water, environmental, pharmaceutical, cosmetic and clinical samples is often complicated by the fact that the microorganism may be present in the sample at concentrations much lower than those of other microorganisms.

Competitor microorganisms, including motile competitors, can often interfere with the detection of a pathogen by overgrowing on the surface of an agar plate or by inhibiting the growth of the particular organism in a culture broth. An isolated colony of the particular organism may not appear on the surface of an agar plate if large numbers of colonies of competitor organisms are present. The competitor organisms may consume essential nutrients and oxygen, release byproducts that possess antibacterial properties, or raise or lower pH to levels which inhibit bacterial growth or kill the organism. As a consequence, the competitor organisms may grow to extremely high concentrations in the culture broth, whereas the bacterial pathogen (e.g. *Listeria*) remains below detectable limits or can actually die off.

An exemplary *Listeria* detection method involves pre-enriching *Listeria* spp. in an enrichment medium and isolating a single colony from said medium. The shape and biochemical characteristics of the isolated single colony can be further analyzed.

There is still the need to further improve the selectivity of such enrichment media. A special aim is to not only enrich all *Listeria* species but also to especially enrich *Listeria monocytogenes* in the presence of other bacteria.

Galbraith et al., J. Appl. Bact. 34(4), 803-813 (1971) have shown that when added to a cell culture long chain fatty acids show a strong antimicrobial effect against certain Gram-positive species while most Gram-negative bacteria are not affected.

It was found now that *Listeria*, especially *L. monocytogenes*, is able to withstand substantially higher concentrations of the compounds like certain fatty acids and other compounds comprising an alkyl chain and a functional group like an acid or OH group compared to other Gram-positive bacteria.

The present invention is therefore directed to a method for enriching and optionally detecting *Listeria* in a sample in the presence of other Gram-positive bacteria comprising incubating the sample with one or more C12 to C16 alkyl acids and/or alkyl alcohols and/or derivatives thereof. The incubation, preferably in a specific medium comprising the said alkyl acids and/or alkyl alcohols and/or derivatives thereof, allows the *Listeria* to replicate and multiply to a detectable level while other microorganisms like other Gram-positive bacteria do not replicate and multiply as effectively as the *Listeria* species.

In one embodiment the *Listeria* to be enriched is *Listeria monocytogenes*.

In a preferred embodiment the incubation takes place at a temperature between 25 to 40° C., preferably between 30 and 37° C.

In another preferred embodiment the incubation is performed for a time between 10 and 60 hours, preferably between 18 to 48 hours.

In a preferred embodiment, detection is done by growing in a selective culture medium, by molecular biological methods like PCR or isothermal amplification technologies, or by immunological technologies like lateral flow or ELISA.

In a preferred embodiment, the alkyl acids and/or alkyl alcohols and/or derivatives thereof are C12 to C16 phosphonic acids, C12 to C16 fatty acids, C12 to C16 dicarboxylic acids, C12 to C16 alcohols or salts thereof. Most preferred are the C14 compounds. Very preferred the compounds have an alkyl chain with no branches and are functionalized at one end of the alkyl chain or at both ends of the alkyl chain with the acid and/or the alcohol group.

The present invention is further directed to a culture medium comprising alkyl acids and/or alkyl alcohols and/or derivatives thereof.

In a preferred embodiment, the alkyl acids and/or alkyl alcohols and/or derivatives thereof are C12 to C16 phosphonic acids, C12 to C16 fatty acids, C12 to C16 dicarboxylic acids, C12 to C16 alcohols or salts thereof.

Most preferred are the C14 compounds, especially myristic acid, salts of myristic acid, tetradecanedioic acid and/or salts thereof, tetradecylphosphonic acid and/or salts thereof as well as 1-tetradecanol.

In a preferred embodiment the medium comprises a second selective agent in addition to the alkyl acids and/or alkyl alcohols and/or derivatives thereof which is not an alkyl acid and/or an alkyl alcohol and/or a derivative thereof.

In a very preferred embodiment the second selective agent reduces or inhibits the growth of Gram-negative bacteria. That means in a preferred embodiment the medium comprises an agent for inhibiting the growth of Gram-negative bacteria.

In a preferred embodiment the medium comprises more than 10 g/l, preferably 10 to 20 g/l of a buffer.

In a preferred embodiment, the buffer is MOPS and/or a phosphate buffer.

In a preferred embodiment the medium comprises the C12 to C16 alkyl acids and/or alkyl alcohols and/or derivatives thereof in concentrations between 10-1000 mg/L.

In one embodiment the medium comprises one or more saccharide components, one or more amino acids, one or more vitamins or vitamin precursors, one or more salts, one or more buffer components, one or more co-factors and one or more nucleic acid components.

In another embodiment, the medium comprises a gelling agent.

In another embodiment, the medium further comprises at least one chromogenic or fluorogenic substrate.

In one embodiment the medium is sterilized.

In another embodiment the medium is in a bag.

The present invention is further directed to a kit for enriching and detecting *Listeria*, the kit comprising a medium as defined above, especially a medium comprising C12 to C16 alkyl acids and/or alkyl alcohols and/or derivatives thereof and means for detecting *Listeria*.

In one embodiment the means for detecting *Listeria* comprises a lysis reagent for lysis of the walls of the cells of the *Listeria*; at least two primers; and optionally at least one DNA-polymerase enzyme for amplifying at least one fragment of the DNA of the *Listeria*.

Figure 1:
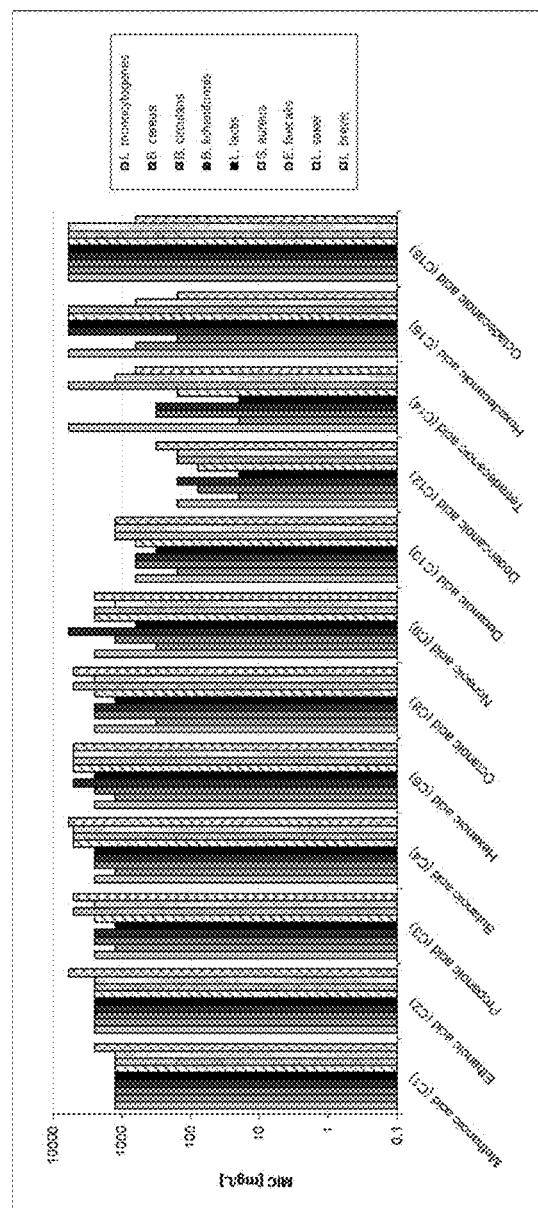
FIGS. 1 to 3 show growth inhibition experiments to demonstrate the applicability of certain fatty acids and other compounds comprising an alkyl chain (C12-C16) and a functional group like an acid or OH group as a selective agent for the enrichment of *Listeria*. Further details can be found in Example 1.

A cell culture is any setup in which cells like microorganisms are cultured. A cell culture medium (synonymously used: culture medium or medium) according to the present invention is any mixture of components which maintains and/or supports the in vitro growth of cells, preferably bacterial cells, more preferred *Listeria*, and/or supports a particular physiological state. In one embodiment, the medium is a chemically defined medium. The cell culture medium can comprise all components necessary to maintain and/or support the in vitro growth of cells or it can be used for the addition of selected components in combination with or not in combination with further components that are added separately (media supplement). Preferably, the cell culture medium comprises all components necessary to maintain and/or support the in vitro growth of cells.

The culture medium can be a liquid medium, a solid medium, like a dry, powdered medium or a dry, granulated medium, or a semi-solid medium like a medium comprising a gelling agent like agar. A person skilled in the art knows how to adapt the certain types of media to be suitable for culturing of the microorganisms. Dry, powdered media or dry, granulated media are for example typically dissolved in aqueous liquids prior to use.

The culture of the cells in the medium can be performed in any container suitable for the culture of cells, such as a petri dish, contact plate, bottle, tube, well, vessel, bag, flask and/or tank. Typically the container is sterilized prior to use.

Culturing is typically performed by incubation of the cells in an aqueous culture medium or a semi-solid culture medium under suitable conditions such as suitable temperature, osmolality, aeration, agitation, etc. which limit contamination with foreign microorganisms from the environment. A person skilled in the art is aware of suitable incubation conditions for supporting or maintaining the growth/culturing of cells.

The cells to be cultured with the medium and according to the method of the invention are bacteria of the genus *Listeria*, synonymously used: *Listeria*, preferably *Listeria monocytogenes*.

The term "sample" comprising the *Listeria* whose growth shall be supported by the methods and media of the present invention can be any type of sample. It can for example be a liquid, semi-liquid or solid sample. Preferably, it is one of the following types of samples:

environmental samples during environmental monitoring of pharmaceutical relevance samples obtained from raw materials, intermediates and/or finished goods of pharmaceutical relevance clinical samples during hospital examinations veterinary samples water samples for examination of drinking and/or waste water and/or swimming pool water food samples for the examination of microbial contamination cosmetic samples Clinical samples may be animal or human samples like body liquids, e.g. blood, urine, feces, sputum etc. or tissue samples. Food samples may be any type of food products and its ingredients such as dairy, vegetable and meat or fish products as well as waste and all manners of raw and processed foods as well as samples taken during processing of food. Environmental samples include environmental material such as surface matter, soil, water and industrial samples. Preferred samples are environmental or food samples.

A selective agent is a compound or a mixture of two or more compounds which inhibits the growth of certain microorganisms, especially of certain bacteria. That means a selective agent does not significantly influence the growth of some bacteria species so that they can replicate and multiply to a detectable level while other bacteria do not replicate and multiply as effectively as the others in the presence of a selective agent. Selective agents to be used in the present invention are especially those which do not significantly influence the growth of *Listeria*. Examples of selective agents are agents which inhibit the growth of Gram-negative bacteria while they do not have a significant influence on the growth of Gram-positive bacteria like LiCl and nalidixic acid. Also the C12 to C16 alkyl acids and alcohols to be used according to the present invention are selective agents.

A cell culture medium or a culture medium which comprises all components necessary to maintain and/or support the in vitro growth of cells typically comprises at least one or more saccharide components, one or more amino acids, one or more vitamins or vitamin precursors, one or more salts, one or more buffer components, one or more co-factors and one or more nucleic acid components (nitrogenous bases) or their derivatives. It may also comprise yeast extract or protein hydrolysates like peptones or tryptones.

Saccharide components are all mono- or di-saccharides, like glucose, galactose, ribose or fructose (examples of monosaccharides) or sucrose, lactose or maltose (examples of disaccharides) or derivatives thereof like sugar alcohols. Saccharide components may also be oligo- or polysaccharides.

Examples of amino acids according to the invention are particularly the proteinogenic amino acids, especially the essential amino acids, leucine, isoleucine, lysine, methionine, phenylalanine, threonine, tryptophan and valine, as well as the non-proteinogenic amino acids such as D-amino acids.

Tyrosine means L- or D-tyrosine, preferably L-tyrosine.

Cysteine means L- or D-cysteine, preferably L-cysteine.

Amino acid precursors and analogues are also included.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid) (including phosphates of ascorbic acid), Vitamin D (Ergocalciferol, cholecalciferol), Vitamin E (Tocopherols, tocotrienols) and Vitamin K (phylloquinone, menaquinones). Vitamin precursors and analogues are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are copper(II) sulphate pentahydrate ($CuSO_4.5\ H_2O$), sodium chloride (NaCl), calcium chloride ($CaCl_2.2\ H_2O$), potassium chloride (KCl), iron(II)sulphate, sodium phosphate monobasic anhydrous ($NaH_2PO_4$), magnesium sulphate anhydrous ($MgSO_4$), sodium phosphate dibasic anhydrous ($Na_2HPO_4$), magnesium chloride hexahydrate ($MgCl_2.6\ H_2O$), zinc sulphate heptahydrate ($ZnSO_4.7\ H_2O$).

Examples of buffers are carbonate, citrate, phosphate, HEPES, PIPES, ACES, BES, TES, MOPS and TRIS, preferably MOPS and/or a phosphate buffer. Phosphate buffer is typically prepared by mixing monosodium phosphate, disodium phosphate and water and adding phosphoric acid to make the pH more acidic or sodium hydroxide to make the pH more alkaline.

MOPS, 3-(N-morpholino)propanesulfonic acid, is a buffer component with a $pK_a$ of 7.20. It is known to a person skilled in the art how to use and prepare buffers with a suitable concentration and pH.

Examples of cofactors are compounds, salts, complexes and/or derivatives of thiamine, biotin, vitamin C, calciferol, choline, NAD/NADP (reduced and/or oxidized), cobalamin, vitamin B12, flavin mononucleotide and derivatives, flavin adenine dinucleotide and derivatives, glutathione (reduced and/or oxidized and/or as dimer), haeme, haemin, haemoglobin, ferritin, nucleotide phophates and/or derivatives (e.g. adenosine phosphates), coenzyme F420, s-adenosyl methionine, coenzyme B, coenzyme M, coenzyme Q, acetyl Co-A, molybdopterin, pyrroloquinoline quinone, tetrahydrobiopterin.

Nucleic acid components, according to the present invention, are the nucleobases, like cytosine, guanine, adenine, thymine, uracil, xanthine and/or hypoxanthine, the nucleosides like cytidine, uridine, adenosine, xanthosine, inosine, guanosine and thymidine, and the nucleotides such as adenosine monophosphate or adenosine diphosphate or adenosine triphosphate, including but not limited to the deoxy- and/or phosphate derivatives and/or dimers, trimers and/or polymers thereof, like RNA and/or DNA.

Compounds may be added which improve the physicochemical properties of the media, like but not limited to, increasing clarity and/or solubility of the media and/or one or more of its components, without significantly negatively affecting the cell growth properties at the concentrations used. Such compounds include but are not limited to chelating agents (e.g. EDTA), antioxidants, detergents, surfactants, emulsifiers (like polysorbate 80), neutralising agents, (like polysorbate 80), micelle forming agents, micelle inhibiting agents and/or polypropylene glycol, polyethylene alcohol and/or carboxymethylcellulose.

The medium typically contains carbohydrates such as sugars and/or sugar mixtures and/or sugar dimers and/or sugar polymers and/or their derivatives. Typically, glucose and/or lactose and/or galactose can be the main carbohydrate sugar components. Glucose is usually included in the medium at a concentration of 0.001 mM to 250 mM in the aqueous medium solution, more preferably 1 mM to 100 mM, even more preferably 5 mM to 50 mM.

Typically, the medium comprises each amino acid in a range from 10 mg to 3 g per liter, preferably in a range from 40 mg to 1 g per liter.

The medium typically comprises vitamins. A typical amount of a vitamin in the medium is in the range of 5 µg to 10 mg per liter, preferably in the range of 50 µg to 6 mg per liter.

Typically, the medium comprises salts. The amount of one type of salts, the trace elements, is typically in the range of 2 µg to 5 mg per liter, preferably in the range of 10 µg to 1.5 mg per liter. Specific salts like Ca, Mg, Na salts may also be present in much higher amounts; the concentration of NaCl can for example be up to 5 to 10 g per liter.

The typical amount of a nucleic acid comprised in the medium is in the range of 0.5 to 10 mg per liter, preferably in the range of 1 to 5 mg per liter.

The medium typically contains all the proteogenic amino acids (and/or their derivatives and/or their conjugates and/or dimers (pure and/or mixed) thereof). It should be noted that the concentrations of the components in the solid medium may differ significantly to those practically measured after dissolution. This is because, for example, certain amino acids can react in the aqueous medium with other components to form products which then indirectly contain the amino acids by which the pure amino acid in solution is thereby depleted. This process may also occur to other easily reactive constituents, for example, but not limited to vitamin C and/or indeed the amino acids may react with each other or with themselves. This process may be an oxidative process dependent on oxygen concentrations and the presence of trace and/or ultra trace elements, in particular the transition metal ions like those of copper and/or iron added directly as components and/or present as contaminants.

Other defined components may also be added to aid detection or identification of microorganisms like indicators.

The culture medium according to the present invention can further comprise at least one chromogenic or fluorogenic substrate. Fluorogenic substrates are complex molecules which, on contact with enzymes synthesized by microorganisms, are cleaved and become fluorescent. The fluorescence emitted is detectable visually and/or with an analytical instrument like a spectrophotometer by illuminating the growth medium using radiation in the UV or visible spectrum. Examples of fluorogenic substrates are fluorescein derivatives (CFA, CFDA), methylumbelliferone derivatives or the fluorescent dye-containing indicator platform Aldols® (developed by the company Biosynth).

Chromogenic substrates are substrates that change their color when they are modified e.g. by a specific enzyme of a microorganism. Examples of chromogenic substrates are ONPG (Ortho-nitrophenyl-β-D-galactopyranoside) or X-Gal (5-bromo-4-chloro-3-indolyl-beta-D-galacto-pyranoside. In this case the medium color after the growth of certain microorganisms of interest will change color and be indicative of such microorganisms.

A typically suitable liquid cell culture medium has a typical composition of 2 to 100 g/L, more preferably 20 to 60 g/L. A medium with a gelling agent has typically an additional weight due to the gelling agent of between 1 and 50 g/L, more preferably between 2 and 30 g/L.

For use of a dry, powdered media or dry, granulated media a solvent, preferably water (most particularly distilled and/or deionized water or purified water or water for injection) or an aqueous buffer is added to the media and the components are mixed until the medium is totally dissolved in the solvent to generate the respective liquid medium.

The solvent is preferably water, preferably deionized water. It may also comprise saline, buffers, soluble acid or base ions providing a suitable pH range (typically in the range between pH 1 and pH 10, preferably around 6.5 to 7.5), stabilizers, surfactants, preservatives, and alcohols or other polar organic solvents as well as gelling agents for the production of semi-solid media.

The media according to the present invention can be stored in any container that is suitable to store liquid or solid media, like a bottle or a bag.

In one embodiment the medium is in a bag, preferably a plastic bag. The bag is tightly sealed so that no air, humidity or contamination can enter. It is also possible to sterilize the medium in the bag by gamma irradiation so that the medium is in a bag and is preferably sterilized.

The media are preferably treated to significantly reduce bioburden load prior to use to such a level that biological contaminants are extremely rarely present in the final, treated medium prior to use. This treatment can be preferably performed in the liquid state by filtration and/or by heat treatment (e.g. 121° C. for 15 minutes) and/or by UV treatment. Gamma irradiation is also possible, especially in the dry state.

The pH of the medium prior to addition of cells is typically between pH 2 and 12, more preferable between pH 4 and 10, even more preferably between pH 6 and 8 and most preferable between pH 6.5 to 7.5 and ideally between pH 7.0 to 7.5.

The culture medium according to the present invention can be used under aerobic as well as anaerobic growth conditions. The person skilled in the art is familiar with the respective measures to be taken for aerobic or anaerobic growth. Typically, for anaerobic culture conditions oxygen is removed, for example by an additive that reduces or preferably eliminates the oxygen in the aqueous medium and/or by a physical means under vacuum and/or by boiling out the oxygen gas. If an additive is used then, preferably, the additive reacts with the oxygen dissolved in the medium to chemically remove is and thus create an anaerobic environment. By whichever means then the container containing the oxygen-depleted medium should prevent fresh oxygen from intruding into the culture medium. The additive may comprise a reducing agent, or may also be an oxygen absorber or scavenger such as a palladium catalyst, or an enzyme, e.g. a mono- and/or di-oxygenase, and/or succinate.

Preferably the medium according to the present invention to be used for enriching *Listeria* in the presence of other bacteria like other Gram-positive bacteria and/or Gram-negative bacteria is a medium which is suitable to effectively support the *Listeria* to grow, replicate and multiply. A person skilled in the art knows how to generate a medium which effectively supports the growth of *Listeria*. There are also commercial media available which support the growth of *Listeria*. Such media can be used as a basis for generating a medium according to the present invention. Examples of suitable media which can be used as a basis for preparing the media according to the present invention are as follows:

| Formula | gm/liter |
|---|---|
| Pancreatic digest of casein | 17.0 |
| Enzymatic digest of soya bean* | 3.0 |
| Sodium chloride | 5.0 |

-continued

| Formula | gm/liter |
|---|---|
| Dipotassium hydrogen phosphate | 2.5 |
| Glucose | 2.5 |
| pH 7.3 ± 0.2 @ 25° C. | |
| or | |
| Tryptone soya broth | 30.0 gm/liter |
| Yeast extract | 6.0 gm/liter |
| Potassium di-hydrogen orthophosphate | 1.35 gm/liter |
| Disodium hydrogen orthophosphate | 9.60 gm/liter |
| Final pH 7.3 ± 0.2 @ 25° C. | |

In any case, beside the one or more compounds to support the growth of *Listera*, the medium of the present invention comprises C12 to C16 linear alkyl acids or alcohols or derivatives thereof. Examples of linear alkyl acids are fatty acids, alkyldicarboxylic acids, also called alkyldioic acids, and alkylphosphonic acids. Examples of preferred derivatives are mono or oligo unsaturated derivatives of the linear alkyl acids or alcohols as well as the anhydrides and salts thereof. Examples of C12 to C16 fatty acids are Lauric acid with the formula $CH_3(CH_2)_{10}COOH$, $CH_3(CH_2)_{11}COOH$, Myristic acid with the formula $CH_3(CH_2)_{12}COOH$, $CH_3(CH_2)_{13}COOH$, Palmitic acid with the formula $CH_3(CH_2)_{14}COOH$ as well as the mono unsaturated derivatives like Myristoleic acid with the formula $CH_3(CH_2)_3CH=CH(CH_2)_7COOH$. Suitable derivatives are salts like the sodium salts or for example fatty acid based ionic liquids. Suitable anhydrides are e.g. myristic anhydride. Suitable alkylphosphonic acids are n-dodecylphosphonic acid, n-tetradecylphosphonic acid, n-hexadecylphosphonic acid. Suitable alkylalcohols are 1-dodecanol, 1-tridecanol, 1-tetradecanol, 1-pentadecanol and 1-hexadecanol. Suitable alkyldicarboxylic acids are dodecanedioic acid, tridecanedioic acid, tetradecanedioic acid, pentadecanedioic acid and hexadecanedioic acid.

Preferably the medium comprises C12 to C16 fatty acids, salts of C12 to C16 fatty acids, C12 to C16 alkylphosphonic acids, C12 to C16 alkylalcohols or C12 to C16 alkyldioic acids, most preferred are the C14 compounds.

Especially preferably the medium comprises myristic acid and/or salts of myristic acid like the sodium salt.

In another preferred embodiment the one or more C12 to C16 alkyl acids and/or alkyl alcohols and/or derivatives thereof are comprised in amounts so that the resulting liquid or semi-liquid medium comprises said C12 to C16 alkyl acids and/or alkyl alcohols and/or derivatives thereof in concentrations between 10 and 1000 mg/L, preferably 200 to 800 mg/L.

In a very preferred embodiment the medium comprises 10 and 1000 mg/L, preferably 200 to 800 mg/L of a C14 component like a C14 alkylacid, a C14 alcohol and/or derivatives thereof, especially of myristic acid and/or a salt of myristic acid like the sodium salt.

In another preferred embodiment the medium comprises one or more other selective agent beside the C12 to C16 alkyl acids and/or alkyl alcohols and/or derivatives thereof. Preferably, the medium comprises one or more selective agents which inhibit the growth of Gram-negative bacteria. Suitable selective agents to inhibit the growth of Gram-negative bacteria are known to the person skilled in the art. Examples are acriflavine hydrochloride, nalidixic acid and lithium chloride.

The present invention is further directed to a method for enriching and optionally detecting *Listeria* in a sample comprising incubating the sample with a medium comprising C12 to C16 alkyl acids and/or alkyl alcohols and/or derivatives thereof. This is done by contacting the sample with said medium. The medium can either be a liquid medium with which the sample is mixed or a semi-solid medium that is contacted with the sample. After mixing or contacting the medium with the sample, the medium is incubated. This is typically done for a certain time at a certain temperature under suitable conditions.

In a preferred embodiment the incubation takes place at a temperature between 25 to 40° C., preferably 30 and 37° C.

In another preferred embodiment the incubation is performed for a time between 10 and 60 hours, more preferred between 18 and 48 hours. Typically, if the detection after the incubation is performed via culturing on a selective culture medium, an incubation of between 10 and 24 hours is sufficient. If the detection is done by molecular biological methods like PCR or immunological methods, a prolonged incubation of more than 24 hours, e.g. between 35 and 50 hours is preferred.

After the incubation, the *Listeria* are typically detected. This can be done by various methods like growing in a selective culture medium, by molecular biological methods like PCR or isothermal amplification technologies, or by immunological technologies like lateral flow or ELISA.

Assays suitable for detection of *Listeria* are for example immunoassays, nucleic acid amplification-based assays, PCR-based assays, nucleic acid hybridization-based assays, bio-sensor assays, immunostaining-microscopy-based assays, nucleic acid-array-based assays, DNA chip-based assays, bacteriophage-detection-based assays, classical microbiology-based assays, and chemical or biochemical assays based on the detection of compounds associated with *Listeria*, enzyme immuno techniques based on chromogene, fluorescence, luminescence, radioactive signal generating response and combinations thereof.

The present invention is further directed to a kit for enriching and detecting *Listeria*. The kit comprise a medium comprising C12 to C16 alkyl acids and/or alkyl alcohols and/or derivatives thereof and means for detecting *Listeria*.

Means for detecting *Listeria* are for example reagents to be used in the one of the detection assays described above like stains, ligands that specifically bind to *Listeria* or primers for PCR based detection.

In one embodiment the means for detecting *Listeria* comprises one or more of the following:
  a lysis reagent for lysis of the walls of the cells of the *Listeria*
  at least two primers and optionally at least one DNA-polymerase enzyme for amplifying at least one fragment of the DNA of the *Listeria*.

The media, kit and method of the present invention provide an effective and easy method for enriching *Listeria* in the presence of other Gram-positive bacteria. C12 to C16 alkyl acids and/or alkyl alcohols and/or derivatives thereof are non-toxic for humans, easy to handle, stable and effectively inhibit the growth of other bacteria beside *Listeria*, especially of other Gram-positive bacteria. Using media according to the present invention which comprise C12 to C16 alkyl acids and/or alkyl alcohols and/or derivatives thereof optionally in combination with other selective agents results in media that can effectively support the growth of *Listeria* while the growth of other Gram-positive bacteria as well as optionally the growth of Gram-negative bacteria is inhibited.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 18181827.9, filed Jul. 5, 2019, are incorporated by reference herein.

EXAMPLES

The following examples represent practical applications of the invention.

Material & Methods

Bacterial Strains and Growth Conditions

The following bacterial strains were selected to cover a representative bacterial diversity: *Listeria monocytogenes* ATCC 13932, *Bacillus cereus* ATCC 11778, *Bacillus circulans*, *Bacillus licheniformis*, *Staphylococcus aureus* ATCC 6538, *Enterococcus faecalis* ATCC 19433, *Lactobacillus sakei* ATCC 15521, *Lactobacillus brevis* and *Lactococcus lactis* ATCC 19435. The bacteria were maintained at −80° C. in glycerol stocks. The bacterial strains were initially cultured on tryptone soy agar (TSA) plates. For testing, the strains were grown overnight in tryptone soya broth (TSB) at respective optimal growth temperatures using a shaking incubator (150 rpm). With the exception of *L. sakei* at 30° C., all strains were incubated at 37° C.

Example 1

Growth Inhibition Experiments

The growth inhibition experiments demonstrate the applicability of certain fatty acids and other compounds comprising an alkyl chain (C12-C16) and a functional group like an acid or OH group as a selective agent for the enrichment of *Listeria*.

Minimum inhibitory (MIC) concentrations of the examined substances were determined by the serial two-fold dilution microtiter plate method in TSB. Overnight cultures were diluted 1:10 in 9 ml TSB and further incubated at their respective optimal growth temperatures for 3 h to ensure that the cells were in the logarithmic growth-phase. These cultures were used to inoculate the serial diluted substances in the microtiter wells at a count of $5 \times 10^5$ CFU/ml each. Subsequently, the 96-well microtiter plates (Corning B.V. Life Science, Amsterdam, Netherlands) were measured at 610 nm wavelength in a TECAN infinite F200 plate reader (Tecan Austria GmbH, Groedig, Austria) to determined potential IL interference. Following incubating for 24 h at the respective optimal growth condition of each strain, sample absorbance at 610 nm was measured a second time. The MIC was defined as the lowest concentration where no bacterial growth could be observed within 24 h.

FIG. 1 shows the MIC of carboxylic acids with alkyl side chain length of 1 to 18 against 9 different Gram-positive bacteria including *L. monocytogenes*. FIG. 1 shows that *L. monocytogenes* can grow in the presence of higher concentrations of carboxylic acids with side chain length of C12-C16 than some of the other Gram-positive bacteria.

Figure 2:
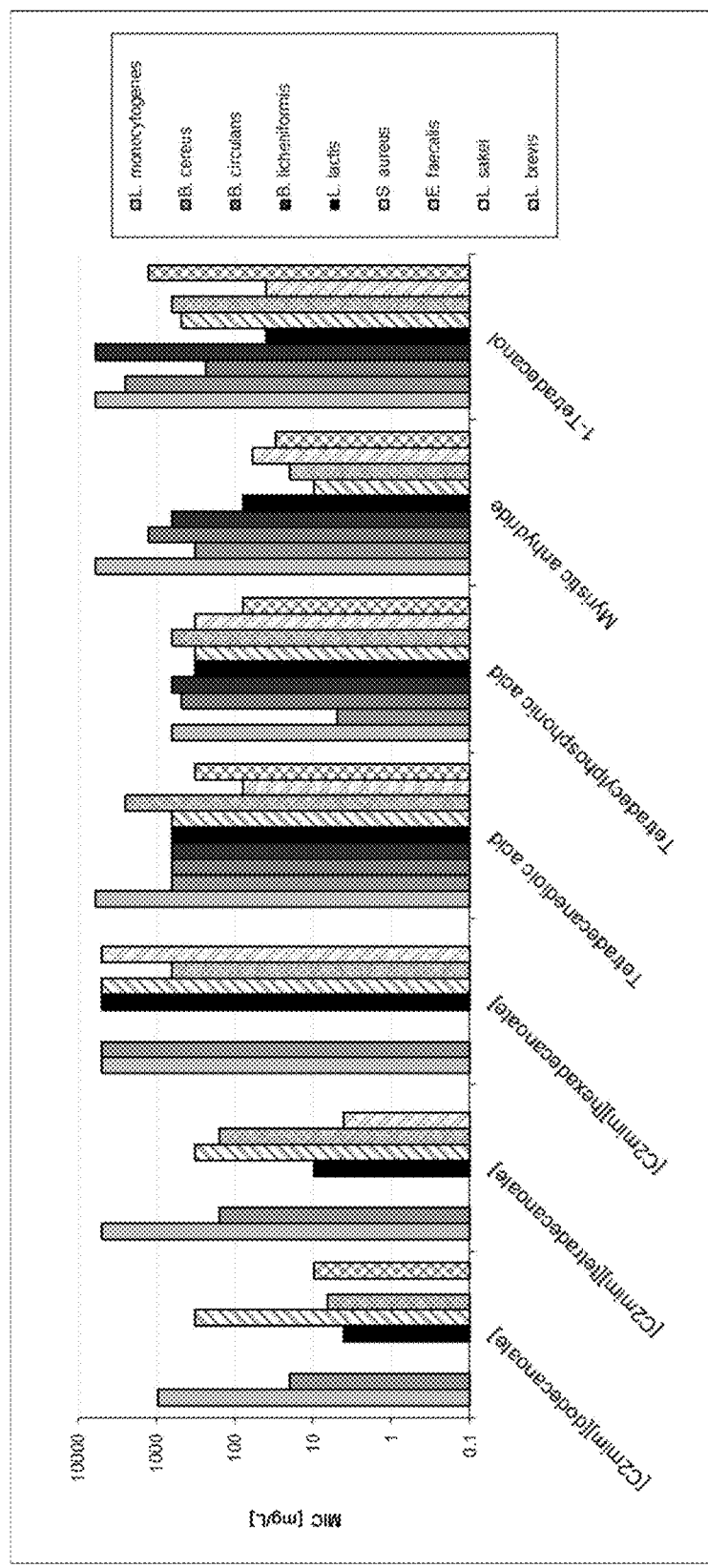

FIG. 2 shows that other compounds comprising an alkyl chain (C12-C16) and a functional group like an acid or OH group and/or derivatives such as salts or anhydrides also allow the growth of *L. monocytogenes* in the presence of higher concentrations than some of the other Gram-positive bacteria.

Figure 3:
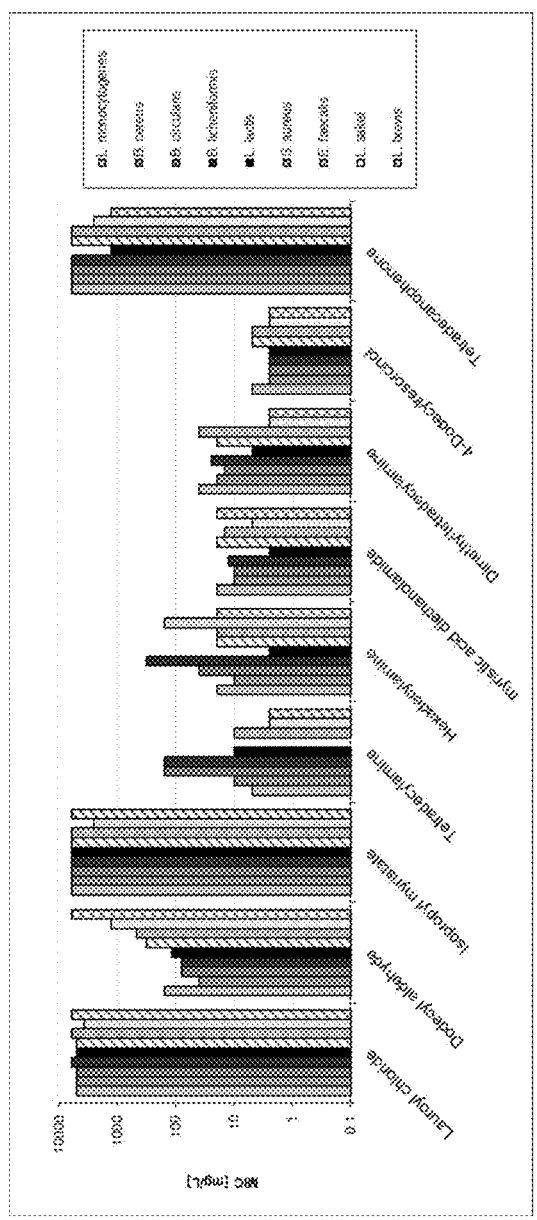

FIG. 3 shows that compounds comprising an alkyl chain (C12-C16) and a functional group like an halide, aldehyde, alkyl ester, amine, amide or an benzyl group do not allow the growth of *L. monocytogenes* in the presence of higher concentrations than some of the other Gram-positive bacteria.

Example 2

Co-Culture Experiments

The co-culture experiments demonstrate the effective improvement of the LE broth by incorporating the respective substances.

The broth used is TSB (Merck KGaA, Germany Art. No. 105459) comprising:
Peptone from Casein (17.0 g/l)
Peptone from Soja flour (3.0 g/l)
D(+)-Glucose Monohydrat (2.5 g/l)
sodiumchlorid (5.0 g/l)
di-potassiumhydrogenphosphate (2.5 g/l)

In these experiments, three different concentrations of *L. monocytogenes* are co-cultured in the presence of either *B. cereus*, *L. lactis*, *S. aureus* or *B. licheniformis*. A growth control for *L. monocytogenes* without a selective agent or a co-culture is included to be able to compare the observed increase in Log CFU numbers for *L. monocytogenes*.

|  | *L. monocytogenes* |  | Co-culture |  |
|---|---|---|---|---|
| Inoculum | low | 6.70E+02 | *B. cereus* | 1.30E+05 |
| [CFU/ml] | middle | 4.40E+04 | *L. lactis* | 3.30E+04 |
|  | high | 5.50E+06 | *Staph. aureus* | 1.10E+06 |
|  |  |  | *B. licheniformis* | 1.50E+06 |

The Experiments are performed with 3 different substances:

| Nr. 12: Tetradecanedioic acid | [468.75 mg/l] |
| Nr. 13: 1-Tetradecanol | [625 mg/l] |
| Nr. 37: Myristic acid | [468.75 mg/l] |

The respective observed growth of *L. monocytogenes* and the respective Co-culture is determined after 24 h of incubation at 37° C.

Figure 4:
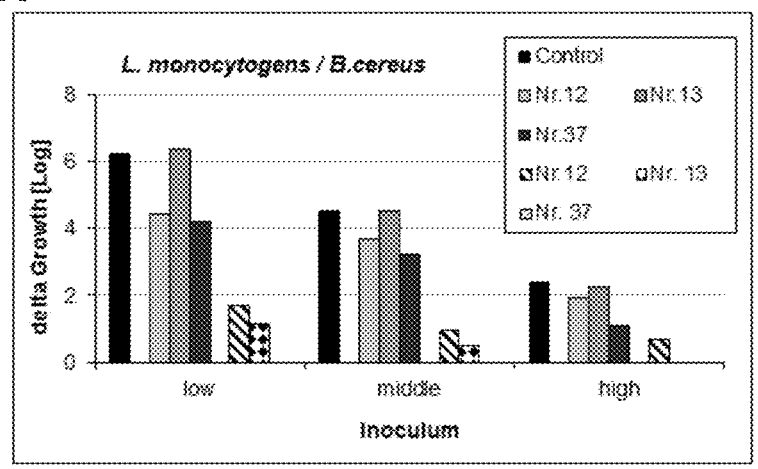
FIGS. 4 and 5 show the growth of *L. monocytogenes* and other microorganisms in an enrichment medium according to the present invention. Further details can be found in Example 2.
Figure 4:
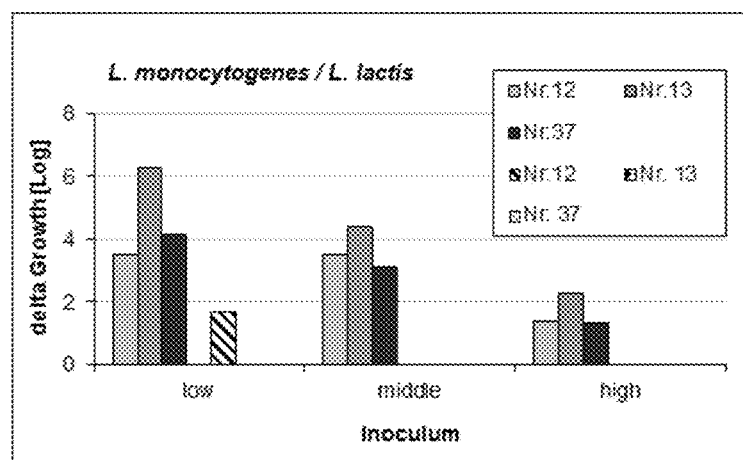

FIG. 4A shows the growth of *L. monocytogenes* (grey bars) and *B. cereus* (structured bars) within 24 h in a co-culture experiment. Growth is expresses as delta growth [Log] compared to the initial inoculum CFU/ml numbers. If no bars are present, no colonies could be counted.

FIG. 4B shows the growth of *L. monocytogenes* (grey bars) and *L. lactis* (structured bars) within 24 h in a co-culture experiment. Growth is expresses as delta growth [Log] compared to the initial inoculum CFU/ml numbers. If no bars are present, no colonies could be counted.

Figure 5:
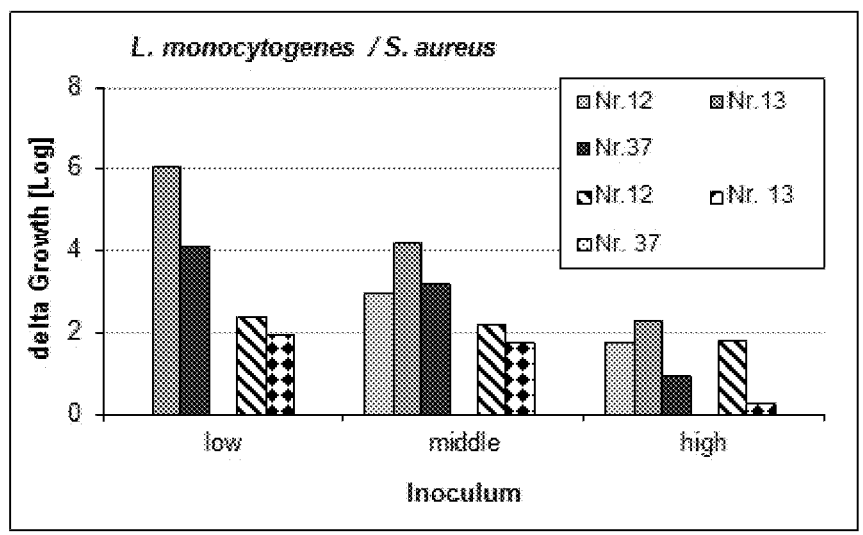
Figure 5:
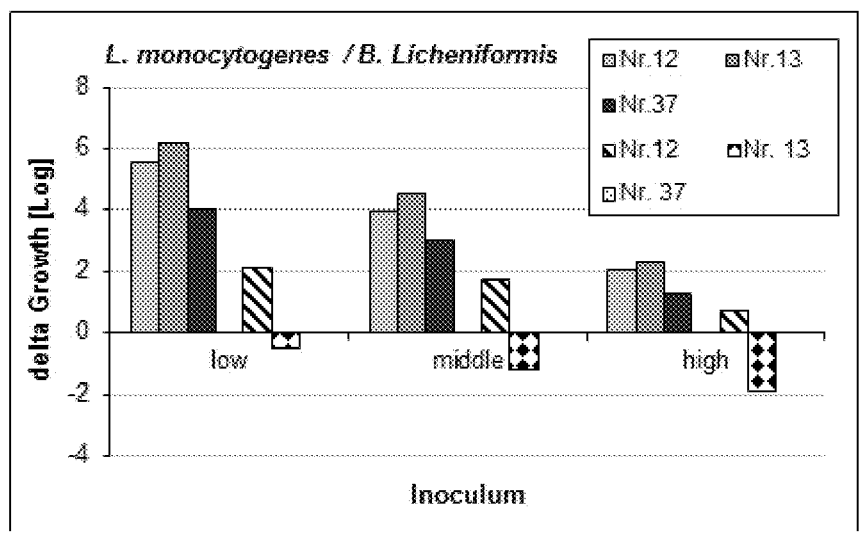

FIG. 5A shows the growth of *L. monocytogenes* (grey bars) and *S. aureus* (structured bars) within 24 h in a co-culture experiment. Growth is expresses as delta growth [Log] compared to the initial inoculum CFU/ml numbers. If no bars are present, no colonies could be counted.

FIG. 5B shows the growth of *L. monocytogenes* (grey bars) and *B. licheniformis* (structured bars) within 24 h in a co-culture experiment. Growth is expresses as delta growth [Log] compared to the initial inoculum CFU/ml numbers. If no bars are present, no colonies could be counted.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method comprising enriching and optionally detecting *Listeria monocytogenes* in a sample in the presence of other Gram-positive bacteria, by incubating the sample in a culture medium comprising one or more $C_{14}$ alkyl acids and/or $C_{14}$ alkyl alcohols, or one or more salts or anhydrides thereof in an amount of 200 to 800 mg/L, and optionally detecting the *Listeria monocytogenes* in the incubated sample.

2. The method according to claim 1, wherein the incubation takes place at a temperature of 25 to 40° C.

3. The method according to claim 1, wherein the incubation is performed for a time of 10 to 60 hours.

4. The method according to claim 1, wherein after said incubation, the detection is done by growing in a selective culture medium, by molecular biological methods or by immunological technologies.

5. The method according to claim 1, wherein the $C_{14}$ alkyl acids and/or $C_{14}$ alkyl alcohols, salts or anhydrides thereof are $C_{14}$ phosphonic acids, $C_{14}$ fatty acids, $C_{14}$ dicarboxylic acids, $C_{14}$ alkyl alcohols, or salts thereof.

6. The method according to claim 1, wherein the *Listeria monocytogenes* is detected in the presence of other Gram-positive bacteria.

* * * * *